(12) United States Patent
Dillingham (10) Patent No.: US 10,864,105 B2
(45) Date of Patent: Dec. 15, 2020

(54) ORTHOPEDIC WRIST BRACE AND SPLINT

(71) Applicant: Sarah Dillingham, Snohomish, WA (US)

(72) Inventor: Sarah Dillingham, Snohomish, WA (US)

( * ) Notice: Subject to any disclaimer, the term of this patent is extended or adjusted under 35 U.S.C. 154(b) by 0 days.

(21) Appl. No.: 16/811,588

(22) Filed: Mar. 6, 2020

(65) Prior Publication Data
US 2020/0281755 A1   Sep. 10, 2020

Related U.S. Application Data (60) Provisional application No. 62/814,858, filed on Mar. 6, 2019.

(51) Int. Cl.
*A61F 5/058* (2006.01)
*A61F 5/01* (2006.01)
*A41D 19/015* (2006.01)

(52) U.S. Cl.
CPC ........ *A61F 5/05866* (2013.01); *A61F 5/0118* (2013.01); *A41D 19/01588* (2013.01)

(58) Field of Classification Search
CPC .... A61F 5/0118; A61F 5/013; A61F 5/05866; A41D 19/015; A41D 19/01582; A41D 19/01588
USPC .................................................... 602/21, 64
See application file for complete search history.

(56) References Cited

U.S. PATENT DOCUMENTS

| | | | |
|---|---|---|---|
| 5,193,771 A * | 3/1993 | Hassel | A47B 21/0371 248/118 |
| 5,417,645 A | 5/1995 | Lemmen | |
| 5,672,150 A * | 9/1997 | Cox | A61F 5/0118 128/879 |
| 5,725,490 A | 3/1998 | Conran | |
| 6,200,286 B1 | 3/2001 | Zamani | |
| 6,835,182 B2 | 12/2004 | Darcey | |
| 6,979,305 B2 * | 12/2005 | Porrata | A61F 5/0118 128/879 |
| 7,364,556 B2 * | 4/2008 | Weaver, II | A61F 5/0118 602/21 |
| 8,235,927 B2 * | 8/2012 | Bauerfeind | A61F 5/0118 602/20 |
| 8,951,217 B2 | 2/2015 | Joseph | |
| 2017/0216078 A1 * | 8/2017 | Rivlin | A61F 5/05866 |
| 2017/0354528 A1 * | 12/2017 | Lane | A61F 5/0118 |

\* cited by examiner

*Primary Examiner* — Keri J Nelson
(74) *Attorney, Agent, or Firm* — Christopher Mayle; Thomas E. LaGrandeur; Bold IP, PLLC (57) ABSTRACT

An orthopedic cock-up wrist brace and splint for people with arthritis, carpal tunnel syndrome, sprains, fractures, tendonitis, repetitive strain injury, osteoporosis, or other wrist injury. The splint having a specially designed hourglass shape formed using medical fit data in addition to established sizing data and refined after comprehensive studies and testing. The splint supplied as a stand-alone product or as part of a wrist brace system.

16 Claims, 9 Drawing Sheets

ORTHOPEDIC WRIST BRACE AND SPLINT

CROSS REFERENCE TO RELATED APPLICATIONS

The following is a non-provisional patent application claiming priority to U.S. provisional patent application 62/814,858 filed on Mar. 6, 2019, which is incorporated by reference in its entirety.

FIELD OF DISCLOSURE

The present invention relates to wrist splints and braces, and more particularly, to an orthopedic cock-up wrist splint made of a lightweight flexible material, perforated to allow for airflow around the wrist, ergonomically shaped to fit left and right hands in a range of sizes, with the option to manufacture using injection molding processes, or customize and 3D print the splint to fit the user's exact hand shape and size, or integrate the splint into a customized support wrap using additive manufacturing processes.

BACKGROUND

Wrist pain is often caused by sudden injuries, such as when a person loses their balance and attempts to brace their fall using their wrist, resulting in a break, fracture, or strain. Wrist injuries can also result from long-term problems, such as repetitive stress injury and carpal tunnel syndrome that may be triggered and worsened through repetitive motions. Wrist pain and injury can also be the result of medical conditions such as tendonitis, osteoarthritis, rheumatoid arthritis, or osteoporosis. Treating wrist pain and injuries often requires a period of rest and restrained motion for the wrist, allowing inflammation in the wrist to subside and for healing to begin. If the wrist is left unrestricted or unsupported, the existing injury can worsen or take longer to heal and chronic conditions are exacerbated. Another problem is that many people sleep with their wrist bent, which may cause more pain and symptoms at night.

Cock-up style wrist braces and splints are intended to securely and comfortably stabilize and protect one's wrist in a neutral position as needed for treating these types of wrist injuries and conditions. However, many of the over the counter braces and splints currently on the market are uncomfortable to wear for any length of time, so users remove them, resulting in low medical compliance and effectiveness.

Most over the counter splints are ambidextrous models offered in one standard size. They are not shaped to the curve of the individual's hand, do not take into account the shapes of the left and right hand, and do not take account of a wide range of hand sizes. Women are heavy users of cock up wrist braces and splints as they are disproportionately affected in the hands and wrists by conditions like arthritis, osteoporosis, and carpal tunnel syndrome, yet few products are designed to fit female hands or target to this market.

Most existing over the counter splints are made of a solid bent strip of metal such as aluminum, but this can be heavy and lack flexibility causing discomfort for the user. Metal splints are not breathable and can cause discomfort through heat and sweating, sometimes leading to skin irritation and rashes. The continuous use of these wrist braces and splints have led to increased intrafunicular pressure, edema, and to some extent, obstruction of the arterial flow, thus prolonging the condition. Thus, exists the need for a unique lightweight, ergonomically shaped, breathable, splint for improved medical function and comfort.

BRIEF DESCRIPTION OF DRAWINGS

The present invention will be described by way of exemplary embodiments, but not limitations, illustrated in the accompanying drawings in which like references denote similar elements, and in which:

FIG. 1 is a perspective view of a left-handed splint in accordance with the present invention in.

SUMMARY

The disclosure presented herein relates to a splint, comprising, a generally hourglass shape including an upper section and a lower section that are connected by a waistline, a distal end, a proximal end, and a concave interfacing surface configured to be mounted to a user's wrist to immobilize or limit motion of the wrist, the splint having an angled bend upward from the lower section, the angled bend at a 20-30 degree angle, one or more airflow passages to improve ventilation and removal of moisture from the surface of the user's skin, wherein the one or more airflow passages are perforations formed through the concave interfacing surface, further comprising a coating on the concave interfacing surface, wherein the coating has heating or cooling properties or is a medicament infused therein for treatment of the user's joint pain, wherein the splint is made of a polyamide (nylon), weighing less than 15 grams, wherein the splint is manufactured using injection molding processes, wherein the splint is designed using a software modeling application and 3D printing process, wherein the splint is removably inserted into a support sleeve, the support sleeve having a dorsal hand section, a palmar hand section, and a wrist section.

The disclosure presented herein also relates to a splint supporting system, comprising a splint, the splint having a generally hourglass shape including an upper section and a lower section that are connected by a waistline, a distal end, a proximal end, and a concave interfacing surface configured to be mounted to a user's wrist to immobilize or limit motion of the wrist, and a support sleeve, the support sleeve having a dorsal hand section, a palmar hand section, and a wrist section, the splint positioned below a top layer of outside fibers of the support sleeve, the splint positioned above one or more layers having moisture-wicking anti-bacterial fibers, further comprising one or more airflow passages on the splint to improve ventilation and removal of moisture from the surface of the user's skin, wherein the one or more airflow passages are perforations formed through the concave interfacing surface, the splint having an angled bend upward from the lower section, the angled bend at a 20-30 degree angle, further comprising a coating on the concave interfacing surface, wherein the coating has heating or cooling properties, or is a medicament infused therein for treatment of the user's joint pain, the support sleeve having additional rigidity on the dorsal side and areas around the thumb for firm support to protect wrist bones, wherein the splint is removably inserted into a section of the palmer hand section, wherein the splint is incorporated into the support sleeve using additive manufacturing processes, wherein the support sleeve is seamless.

The preceding and following embodiments and descriptions are for illustrative purposes only and are not intended to limit the scope of this disclosure. Other aspects and advantages of this disclosure will become apparent from the following detailed description.

DETAILED DESCRIPTION

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined).

"Exemplary" is used herein to mean "serving as an example, instance, or illustration." Any aspect described in this document as "exemplary" is not necessarily to be construed as preferred or advantageous over other aspects Throughout the drawings, like reference characters are used to designate like elements. As used herein, the term "coupled" or "coupling" may indicate a connection. The connection may be a direct or an indirect connection between one or more items. Further, the term "set" as used herein may denote one or more of any item, so a "set of items" may indicate the presence of only one item or may indicate more items. Thus, the term "set" may be equivalent to "one or more" as used herein.

In the following detailed description, numerous specific details are set forth in order to provide a more thorough understanding of the one or more embodiments described herein. However, it will be apparent to one of ordinary skill in the art that the invention may be practiced without these specific details. In other instances, well-known features have not been described in detail to avoid unnecessarily complicating the description.

Figure 1:
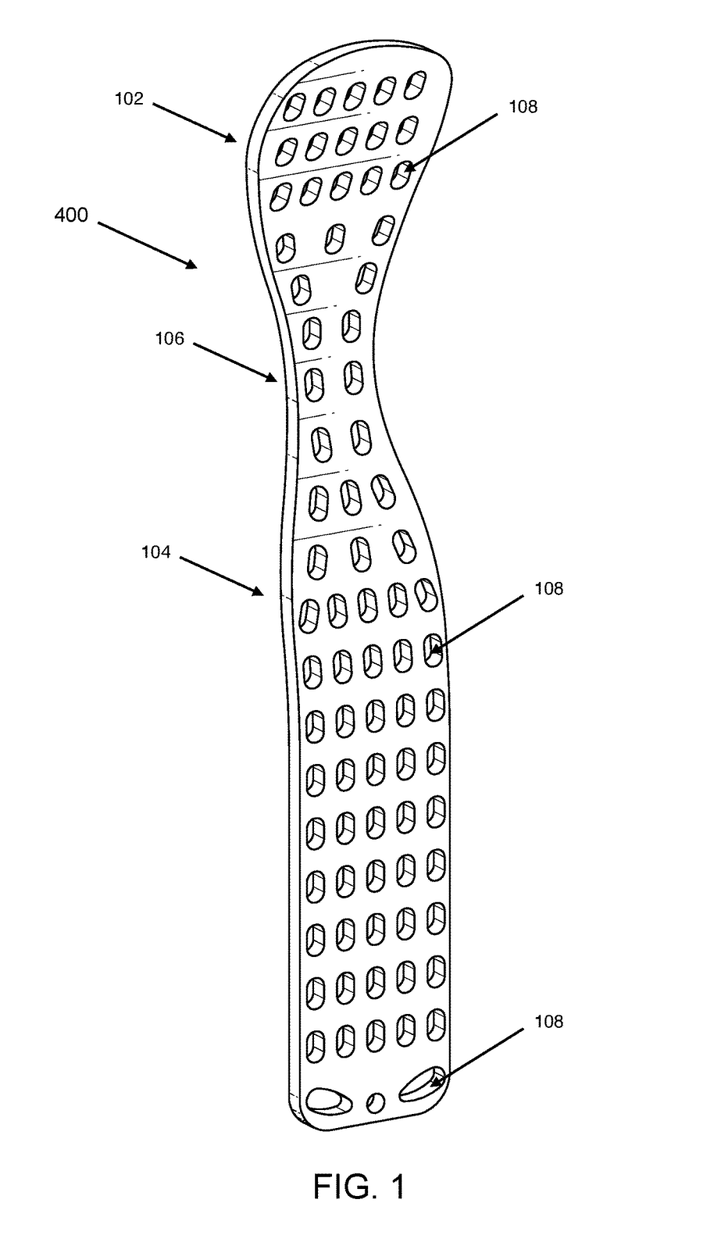
Figure 2:
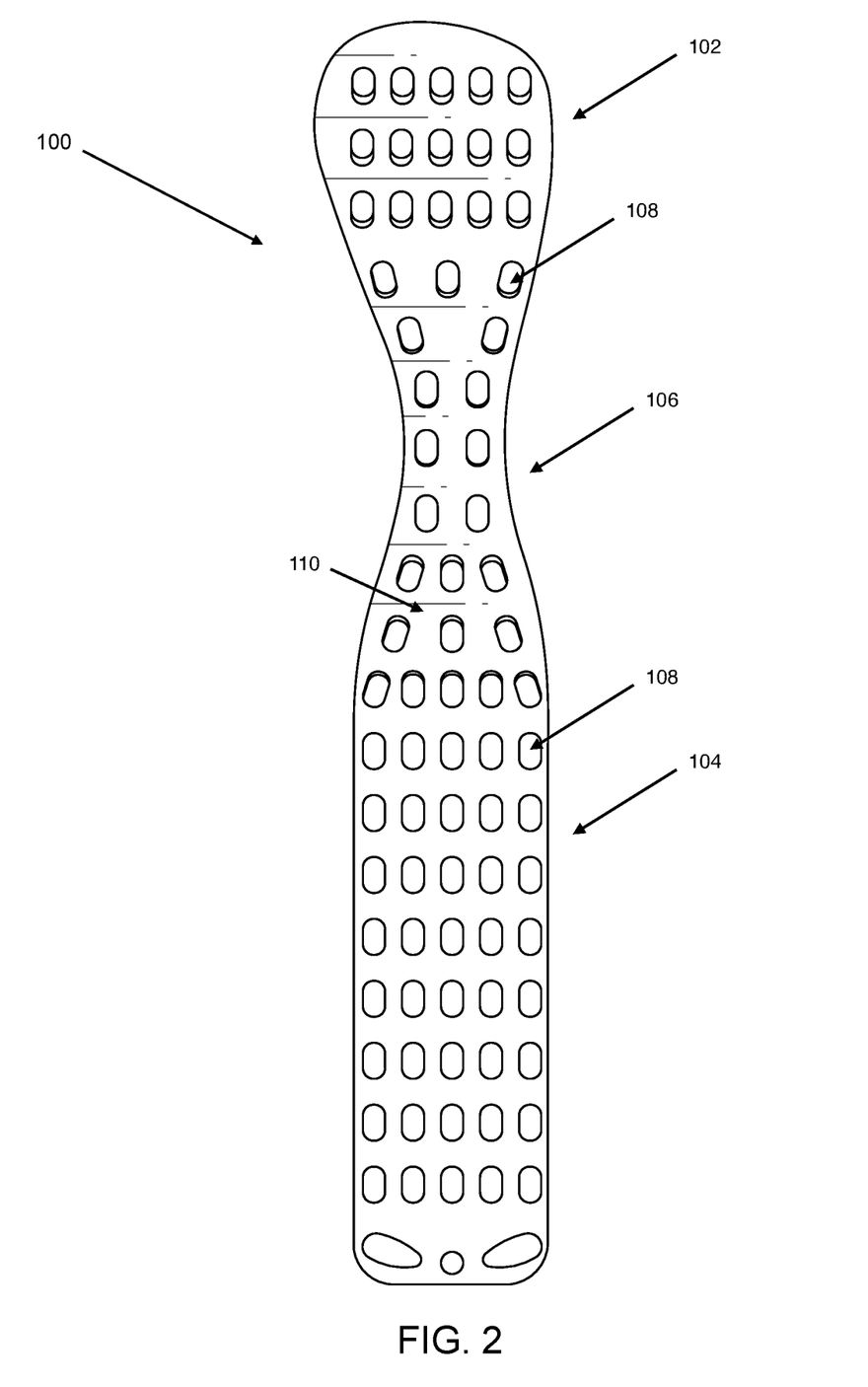
FIG. 2 is a front view of the right-handed splint.
Figure 3:
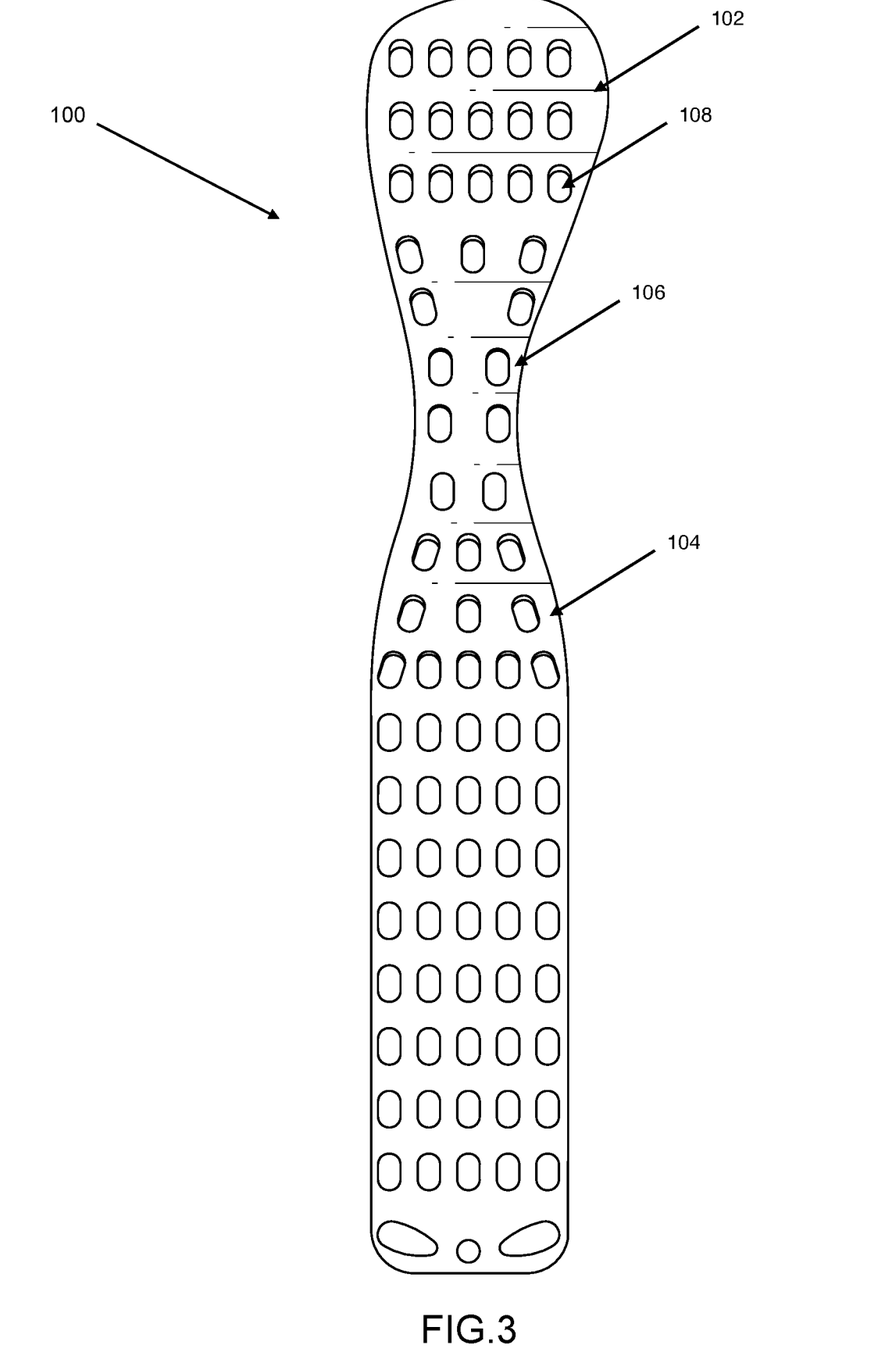
FIG. 3 is a rear view of the right-handed splint.
Figure 4:
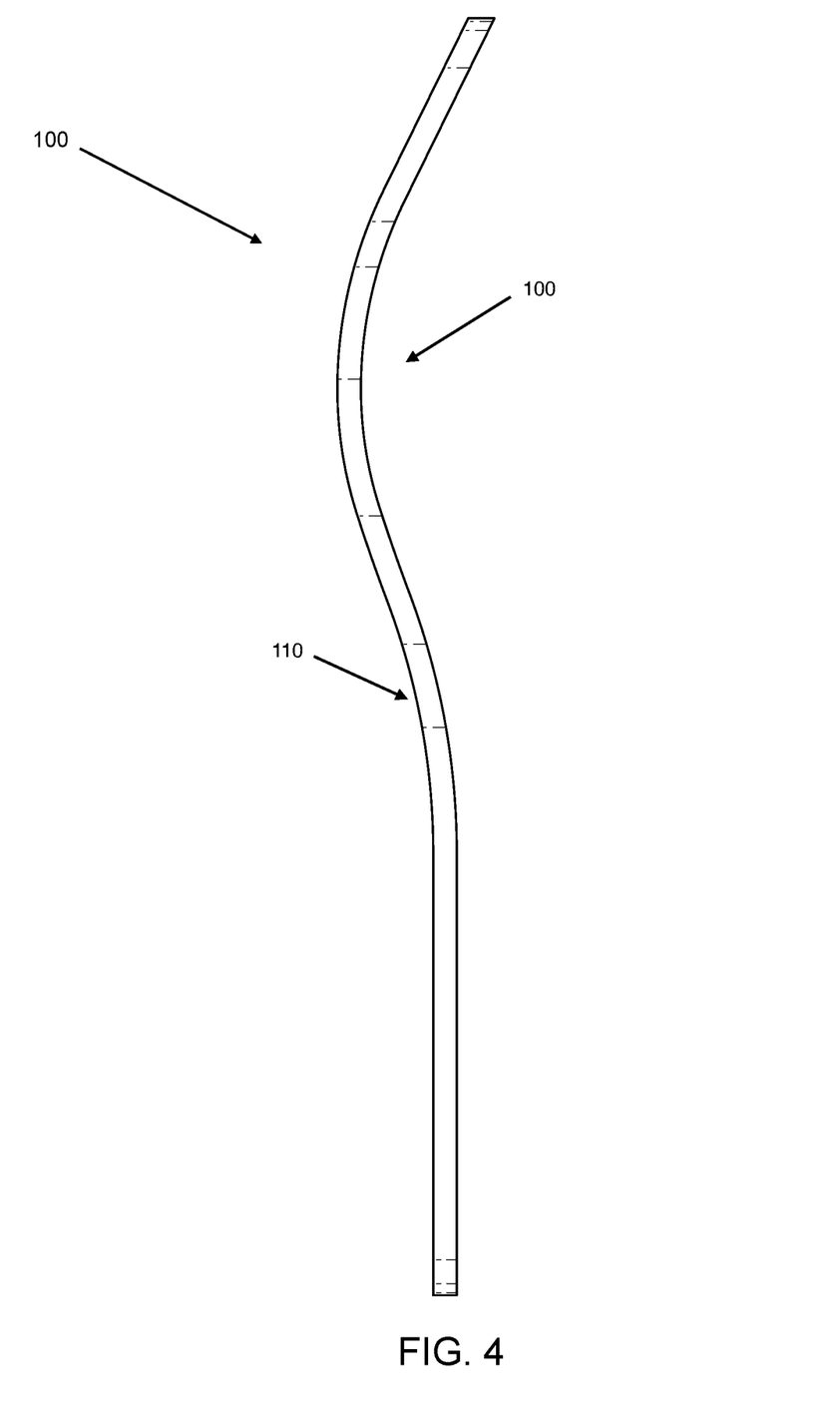
FIG. 4 is a left side view of the right-handed splint.
Figure 5:
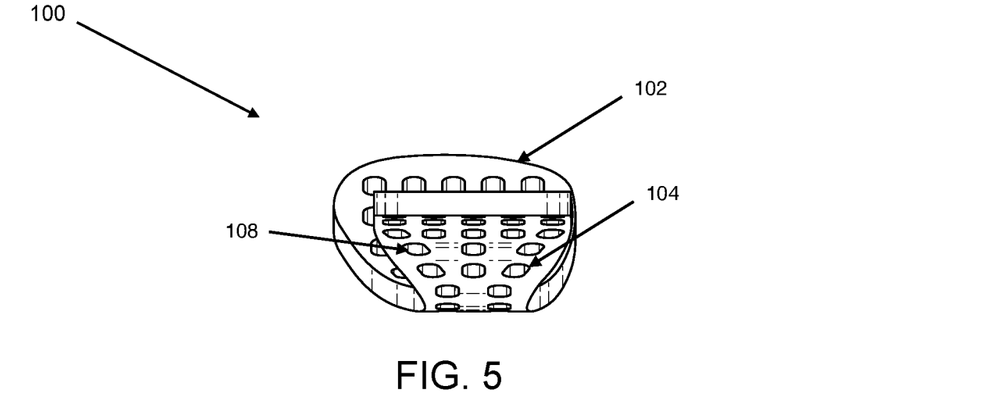
FIG. 5 is a bottom perspective view of the right-handed splint.
Figure 6:
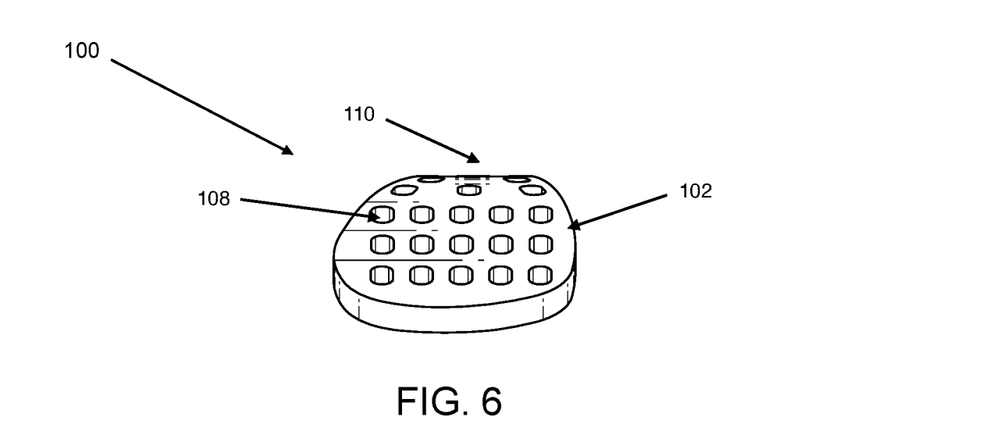
FIG. 6 is another perspective view of the right-handed splint.

The present disclosure is generally drawn to a system and method, according to one or more exemplary embodiments, for an orthopedic cock-up wrist brace and splint for people with arthritis, carpal tunnel syndrome, sprains, fractures, tendonitis, repetitive strain injury, osteoporosis, or other wrist injury. The splint was designed using medical fit data in addition to the established sizing data and refined after comprehensive studies and testing. The splint can be supplied as a stand-alone product or as part of a wrist brace system. The position, size and shape of perforations have been designed to offer stability and support, with a small degree of flexibility such as if the user should fall, the splint will not shatter or break, reducing the risk of injury With reference now to FIG. 1 a left-handed exemplary embodiment of the system according to the present invention is generally designated. The system includes a left-handed splint, such as splint 400. The word "splint" is not meant to be limiting and may include "cast" or "brace" or derivatives thereof and words of similar import. FIGS. 2-6 illustrate a right-handed splint 100. Splint 100 comprises a generally hourglass shape including an upper section such as upper section 102 and a lower section such as lower section 104 that are connected by a waistline such as waistline 106. Splint 100 may further include a distal end, a proximal end, and a concave interfacing surface such as interfacing surface 110, as illustrated in FIGS. 2 and 4, with a 20-degree upward bend from lower section 104, and a convex rear surface on the palmar side facing opposite of the user's wrist. However in some in embodiments the angle be any degrees such as between 20 to 30 degrees. Interfacing surface 110 may be configured to be mounted to the user's wrist to immobilize or limit motion. In the preferred embodiment, splint 100 measures 0.8 mm by 26.1 mm by 174.3 mm. Interfacing surface 110 may be ergonomically shaped to help with fitment of splint 100 to the user's wrist while also minimizing shifting of the wrist along or within splint 100.

Splint 100 may be supplied in a left or right-hand model as required by the user, or an ambidextrous model if preferred. Splint 100 may include a coating applied to interfacing surface 110. Interfacing surface 110 may be coated, for instance with a coating that has heating or cooling properties or a medicament infused therein for treatment of the user's joint pain. Heating or cooling properties may entail an additional coating to create a sensation of warmth or cold to reduce joint pain and inflammation such as but not limited to gels, foams or paints that create a cooling sensation, when stored in a cooling container such as a freezer, or otherwise activated; gels, foams or paints that create a warming heating sensation once they are heated in a microwave, or otherwise activated; or gels or paints that create a warming sensation through electrical conduction.

The Figures only depict left and right handed embodiments; however, the splint may be any configuration that is able to substantially immobilize the wrist to a range of motion preferred by the physician whilst retaining the medically approved position of 20 degree upward bend of the user's wrist.

Splint 100 is preferably made of high strength material that is lightweight and retains flexibility within medically effective parameters. Splint 100 may be comprised of polyamide (nylon), polymethyl methacrylate (acrylic), resins or other polymers. In one or more preferred embodiments the material is polyamide (nylon). Splint 100 may also be made of acrylonitrile butadiene styrene thermoplastic polymer, carbon fiber, lightweight plastic or polymer-based material, or other lightweight material. In one or preferred embodiments, splint 100 weighs under 15 grams. Splint 100 offers superior rigidity and strength (tested against a maximum stress recorded of $3.296e+007 N/m^2$ with the tensile stress of the material being $4.070e+007 N/m^2$. The test found that there is no failure and no deformation of the material), making it ideal for weight-bearing splints for a user's wrists.

Splint 100 may include one or more airflow passages to improve ventilation and removal of moisture from the surface of the hand, arm, and wrist. The airflow passages may be in the form of one or more perforations, such as perforations 108 along the body of splint 100 having a plurality of apertures throughout the body of splint 100. Perforations 108 are designed and arranged to retain the rigidity of the splint. Perforations 108 allows fresh air to circulate through the body to wick away sweat as well as built up moisture, reducing the risk of discomfort and rashes. The pattern of perforations 108 is not limited and may have any geometric pattern or be arranged to depict any number of symbols or designs. For example perforations may be round, oval or hexagonal shaped.

Splint 100 may be designed using a software modeling application and 3D printing process with one or more computing devices whereby splint 100 may be customizable in size. The software modeling application and 3D printing process allows for the uploading, manipulation, alignment, and creation of splint 100 using the user's measurements from x-rays or other radiographs, 3D models of the specific user's wrist, a mold, or direct numerical references obtained by the user or by a trained professional, whereby the measurements are imported and overlaid upon an existing 3D model in a software modeling application and adjusted accordingly. The 3D printing process may include 3D mapping, digitalization, and templating performed on the hands, wrist, and arms of a user, whereby using the software modeling application, an ergonomically fitted splint 100 may be fabricated that can be personalized and customized to fit the user's exact wrist and hand shape. Software modeling application may be utilized to calculate and adjust the flexibility and rigidity requirements so that they are within the correct medical range. Variable colors and designs based on user preferences for ornamental, indicia, or clinical purposes can be produced. In other non-limiting embodiments splint 100 may be manufactured via injection molding processes whereby the product may be offered in a range of pre-formed sizes.

Figure 7:
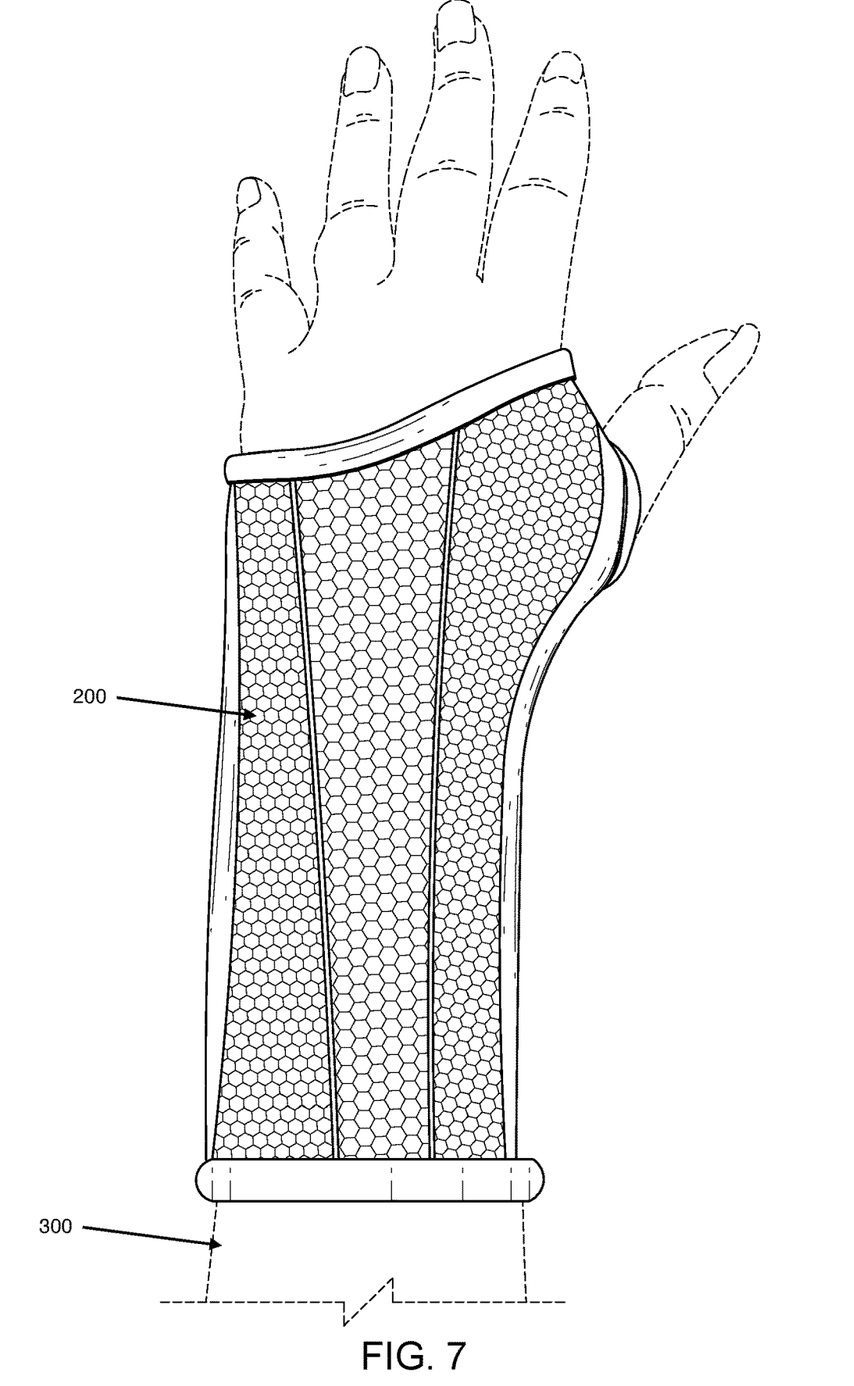
FIG. 7 is a top view of a left-handed support sleeve.
Figure 8:
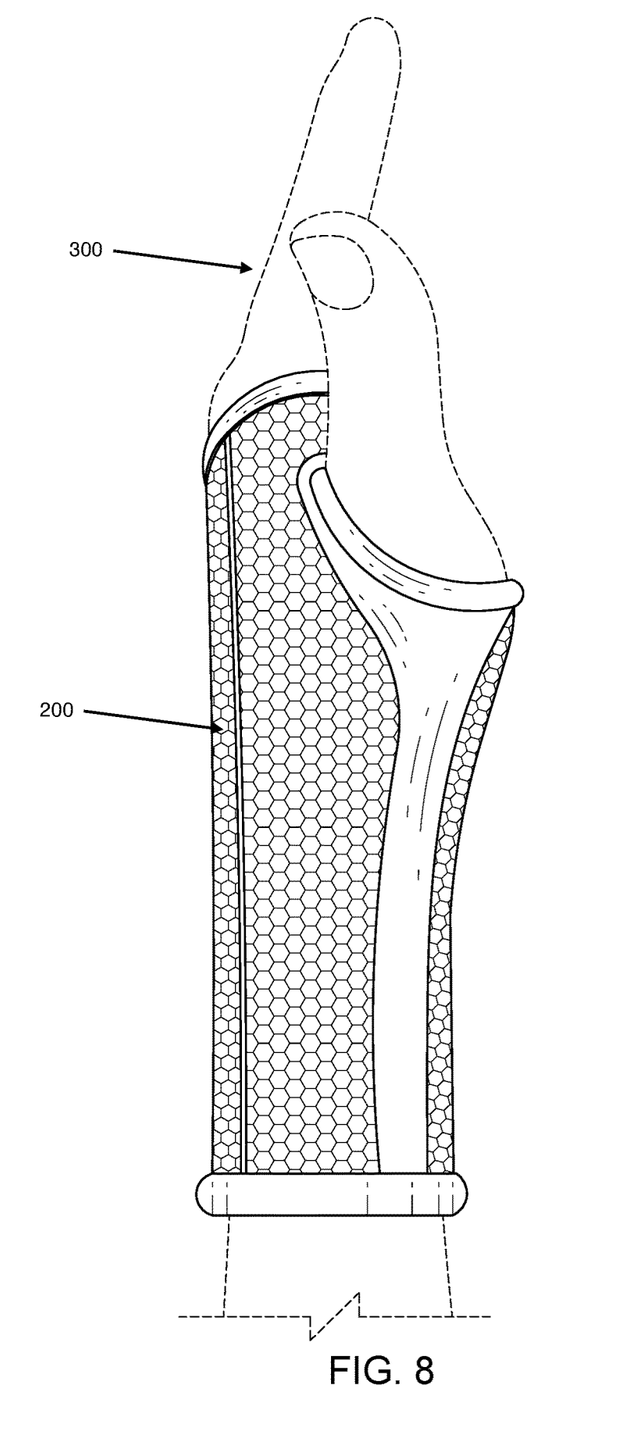
FIG. 8 is side view of the left-handed support sleeve.

In one or more non-limiting embodiments, the splint may be incorporated into a glove like support sleeve using additive manufacturing processes such as left handed support sleeve 200, as illustrated in FIG. 7-8, to provide additional compression and support for the painful and inflamed areas of a user's wrist and hand, such as user 300. Support sleeve 200 is tailored and constructed so that it provides additional thumb support and does not chafe knuckles. Support sleeve 200 may have a dorsal hand section, a palmar hand section, and a wrist section. Support sleeve 200 may be seamless and use the density of knit stitches combined with yarns that have the properties of stretch, rigidity, compression, microbial, anti-bacterial, heating, cooling, anti-inflammatory, and moisture wicking to provide compression, support, stability, and comfort to the user. Support sleeve 200 may have additional rigidity on the dorsal side and additional areas, such as near or around the thumb, for firm support to protect wrist and thumb bones.

In one or more non-limiting embodiments, splint 100 may be designed and produced using injection molding production techniques.

Figure 9:
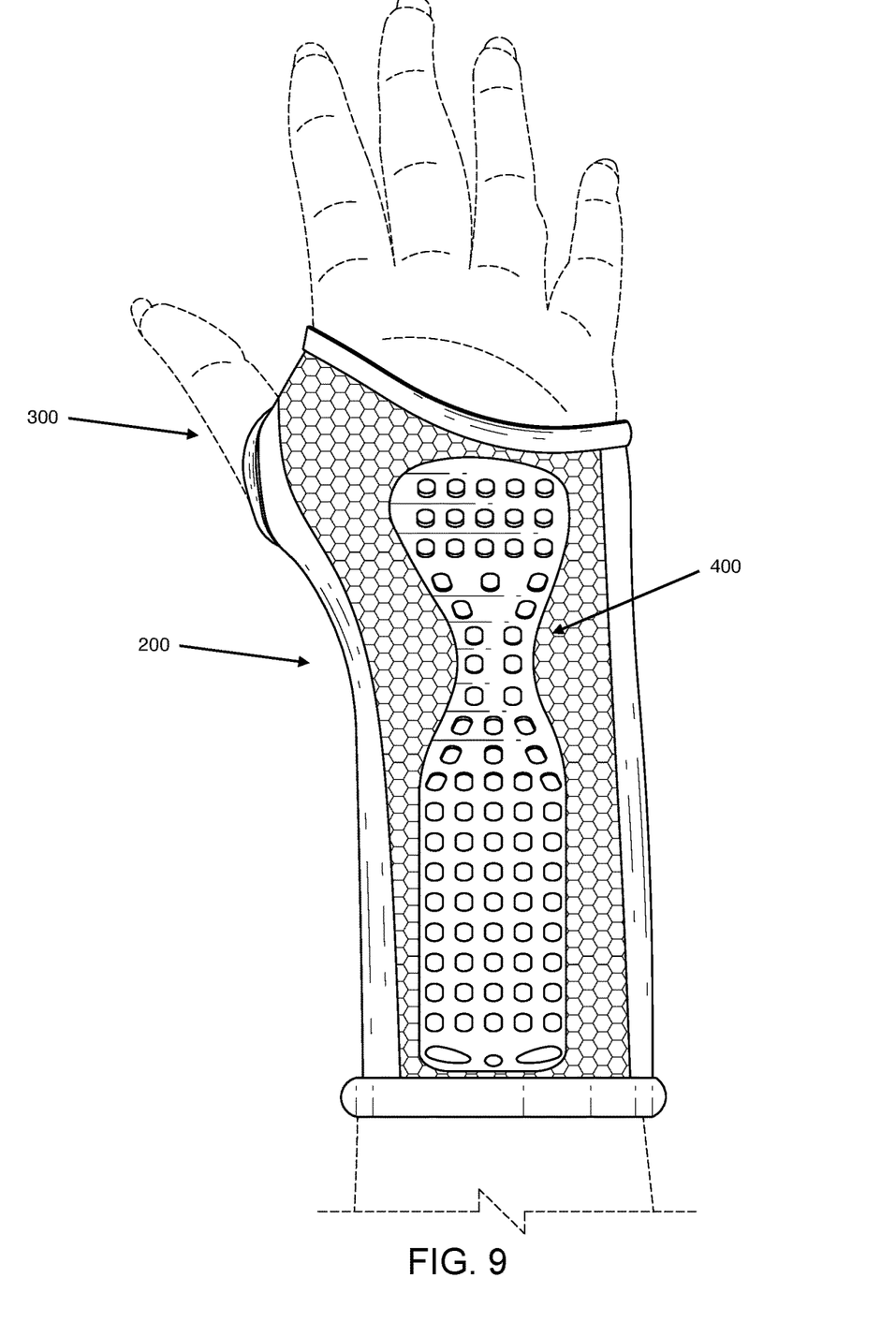
FIG. 9 is a bottom cross sectional view of the left-handed support splint inside the left-handed support sleeve.
Figure 10:
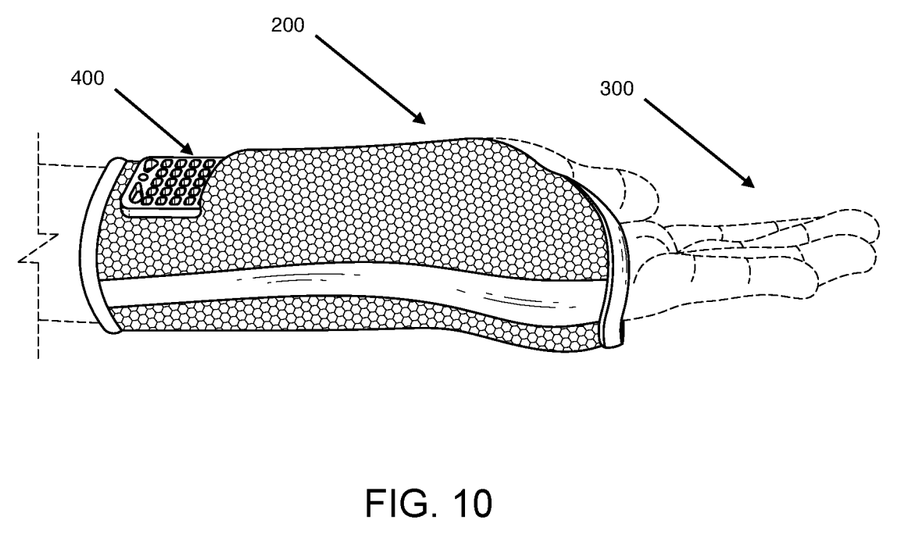
FIG. 10 is a side view of a left-handed splint inside the left-handed support sleeve.

A splint, such as splint 400, the left-handed variation of splint 100, may be removable, held in a section of the palmar side of support sleeve 200, as illustrated in FIG. 9-10, where splint 400 may be found one layer down from the top layer of the outside fibers of support sleeve 200 but above inner layers having moisture-wicking anti-bacterial fibers. In one or more embodiments, splint 400 may be knitted or sewn into the support sleeve as a non-removable integral part. In one or more embodiments, splint 400 may be secured in the support sleeve with a fastener, such as a button, strap, zipper, Velcro or any other fastening means. While knitted or secured into support sleeve 200, splint 400 may be orientated to keep the user's 300 hand and wrist in the medically correct cock-up position with additional rigid areas on the dorsal side of support sleeve 200 to restrict the user's 300 range of upward motion.

The foregoing description of the invention has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the use contemplated. The scope of the invention is to be defined by the claims.

What is claimed is:

1. A splint, comprising:
a generally hourglass shape including an upper section and a lower section that are connected by a waistline, a distal end, a proximal end, and a concave interfacing surface ending at a top of the upper section configured to keep a hand and a wrist of a user in a medically correct cock-up position, the splint having an angled bend upward from the lower section, the upper section having an asymmetrical shape characterized by a first side curve contour and a second side curve contour opposite of the first side curve contour, the first side curve contour greater than the second side curve contour, the first side curve contour extending vertically beyond the second side curve contour at the top of the upper section.

2. The splint of claim 1, the angled bend at a 20-30 degree angle, the splint having a 26.1 mm width by 174.3 mm height.

3. The splint of claim 1, shaped to ergonomically fit a left hand or a right hand of the user, the upper section dependent on which hand the splint is to be placed upon wherein the first side curve contour for the left hand is on the left side of the concave interfacing surface and the first side curve contour for the right hand is on the right side of the concave interfacing surface.

4. The splint of claim 3 further comprising: one or more airflow passages to improve ventilation and removal of moisture from the surface of the user's skin, wherein the one or more airflow passages are perforations formed through the concave interfacing surface on the upper section and the lower section of the splint.

5. The splint of claim 4 further comprising: a coating on the concave interfacing surface.

6. The splint of claim 5, wherein the coating has cooling or heating properties.

7. The splint of claim 5, wherein the coating is a medicament infused therein for treatment of the user's joint pain.

8. The splint of claim 4, wherein the splint is made of polyamide (nylon) weighing less than 15 grams.

9. The splint of claim 4, wherein the splint is designed and manufactured using injection molding production processes.

10. The splint of claim 4, wherein the splint is designed and manufactured using a software modeling application and 3D printing process.

11. The splint of claim 4, wherein the splint is non-removable and integrated into a support sleeve through knitting, sewing, adhesives or by using additive manufacturing processes.

12. The splint of claim 4, wherein the splint is removably inserted into a support sleeve, the support sleeve having a dorsal hand section, a palmar hand section, and a wrist section.

13. A splint supporting system, comprising:

a splint, the splint having a generally hourglass shape including an upper section and a lower section that are connected by a waistline, a distal end, a proximal end, and a concave interfacing surface ending at a top of the upper section configured to keep a hand and a wrist of a user in the medically correct cock-up position, the splint having one or more airflow passages on the upper section and the lower section of the splint to improve ventilation and removal of moisture from a surface of the user's skin, wherein the one or more airflow passages are perforations formed through the concave interfacing surface;

a support sleeve, the support sleeve having a dorsal hand section, a palmar hand section, and a wrist section;

the splint positioned below a top layer of outside fibers of the support sleeve, the splint positioned above one or more layers having moisture-wicking anti-bacterial fibers, the splint having an angled bend upward from the lower section, the angled bend at a 20-30 degree angle, the upper section having an asymmetrical shape characterized by a first side curve contour and a second side curve contour opposite of the first side curve contour, the first side curve contour greater than the second side curve contour.

14. The splint supporting system of claim 13, further comprising: a coating on the concave interfacing surface, wherein the coating has heating or cooling properties or has a medicament infused therein for treatment of the user's joint pain.

15. The splint supporting system of claim 14, the support sleeve having additional rigidity on the dorsal hand section and areas around the thumb for firm support to protect the wrist and thumb bones.

16. The splint supporting system of claim 15, wherein the splint is removably inserted into a section of the palmer hand section, the first side curve contour extending vertically beyond the second side curve contour at the top of the upper section, the upper section dependent on which hand the splint is to be placed upon wherein the first side curve contour for the left hand is on the left side of the concave interfacing surface and the first side curve contour for the right hand is on the right side of the concave interfacing surface.

* * * * *